United States Patent
Estrada Garcia et al.

(10) Patent No.: US 8,852,601 B2
(45) Date of Patent: Oct. 7, 2014

(54) METHOD OF STIMULATING GROWTH AND RESISTANCE TO DISEASES OF AQUATIC ORGANISMS

(75) Inventors: Mario Pablo Estrada Garcia, Ciudad de la Habana (CU); Rebeca Martinez Rodriguez, Ciudad de la Habana (CU); Amilcar Arenal Cruz, Camaguey (CU); Rafael Marcos Pimentel Pérez, Camaguey (CU); Antonio Morales Rojas, Ciudad de la Habana (CU); Eulogio Pimentel Vázquez, Camaguey (CU); Alexander Espinosa Vázquez, Camaguey (CU); Carmen Aday Garcia Molina, Camaguey (CU); Edenaida Cabrera González, Camaguey (CU); Mirta Vinjoy Campa, Ciudad de la Habana (CU); Sergio Toledo Pérez, Ciudad de la Habana (CU); Olimpia Carrillo Famés, Ciudad de la Habana (CU); Claudina Zaldivar Muñoz, Ciudad de la Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 2437 days.

(21) Appl. No.: 10/501,697

(22) PCT Filed: Jan. 22, 2003

(86) PCT No.: PCT/CU03/00002
§ 371 (c)(1),
(2), (4) Date: Apr. 11, 2005

(87) PCT Pub. No.: WO03/080102
PCT Pub. Date: Oct. 2, 2003

(65) Prior Publication Data
US 2006/0234905 A1    Oct. 19, 2006

(30) Foreign Application Priority Data
Jan. 24, 2002 (CU) .................................. 2002/0020

(51) Int. Cl.
| | | |
|---|---|---|
| A61K 39/00 | (2006.01) |
| C12N 15/09 | (2006.01) |
| C07K 7/06 | (2006.01) |
| A23K 1/18 | (2006.01) |
| A61K 38/25 | (2006.01) |
| A61K 38/08 | (2006.01) |
| A23K 1/165 | (2006.01) |
| A23K 1/16 | (2006.01) |

(52) U.S. Cl.
CPC . *C07K 7/06* (2013.01); *A23K 1/188* (2013.01); *A61K 38/25* (2013.01); *A61K 38/08* (2013.01); *A23K 1/165* (2013.01); *A23K 1/1631* (2013.01)
USPC ........................................ 424/185.1; 435/69.4

(58) Field of Classification Search
None
See application file for complete search history.

(56) References Cited

U.S. PATENT DOCUMENTS

| | | | | |
|---|---|---|---|---|
| 4,411,890 A | * | 10/1983 | Momany | ........................ 514/17 |
| 4,880,778 A | | 11/1989 | Bowers et al. | |
| 5,486,505 A | | 1/1996 | Bowers et al. | |
| 5,767,124 A | | 6/1998 | Kaufman et al. | |
| 5,773,441 A | * | 6/1998 | Hipskind et al. | ......... 514/253.09 |
| 5,972,895 A | * | 10/1999 | Braswell et al. | ................ 514/17 |

FOREIGN PATENT DOCUMENTS

| | | | |
|---|---|---|---|
| ES | 2 005 224 A | | 3/1989 |
| WO | 00759 | * | 1/1994 |

* cited by examiner

*Primary Examiner* — Debbie K Ware
(74) *Attorney, Agent, or Firm* — Hoffmann & Baron, LLP

(57) ABSTRACT

The invention is related with the chemical synthesis for increase the growth rate in marketable fish and crustacean
The aim of this invention is supply GHRP-6 to induce directly or indirectly the release of growthing hormone or like, to produce the increase of circulating growthing hormone level in the blood of the fishes. The peptide is stable, soluble and biologically active.
The peptide is able to stimulate growth, improve the larvae quality, and increase the defense against pathogen agents, the dry weight, the protein concentration and the RNA in muscle of fish and crustaceans.

14 Claims, 8 Drawing Sheets

METHOD OF STIMULATING GROWTH AND RESISTANCE TO DISEASES OF AQUATIC ORGANISMS

This application is the U.S. National Phase of International Application Number PCT/CU03/00002 filed on 22 Jan. 2003, which is incorporated herein by reference.

BACKGROUND OF THE INVENTION

The invention is related with the chemical synthesis for increase the growth rate in marketable fish and crustacean. The synthesis of peptide analogs of Leu and Met enkephalins was reported and showed that they stimulated growth hormone (GH) release in animals (Bowers C, Momany, G, Reynolds G and A. Hong. 1984. On the in vitro and in vivo activity of a new synthetic hexapeptide that acts on the Pituitary to specifically release growth hormone. Endocrinology. 114: 1537-45).

Studies to investigate structure-activity relationships of GH releasing peptides (GHRPs) continued and let to the identification of GHRP-6 (His-D-Trp-Ala-Trp-D-Phe-Lys-$NH_2$) (SEQ. ID. NO.: 1), who has been demonstrated to be an extremely potent and safe GH secretagogue (GHS) in animals, including humans, however no previous report has been published using this compound in aquatic organisms.

We demonstrated as a novel fact, taking into account the lack of evidence crustaceans of the signal cascade to stimulate growth (hypothalamus—pituitary gland—target organ), that the peptide GHRP-6 alone is able to exert a similar biological function in crustaceans than in mammals.

Fresh water fish is the principal production in aquaculture, nevertheless in the last decade the increasing of culture of marine algae, mollusks and crustaceans had been significantly. The improving knowledge of the genetic, reproduction, nutrition and the physiology of the organisms to cultivate is the first step to improve the aquaculture production (Gómez-Chiarri M, Smith G J, de la Fuente J and Powers D A. 1998 Gene transfer in shellfish and algae. In de la Fuente J and Castro F O, editors. Gene transfer in aquatic organisms. Austin, Tex.: R G Landes Company and Germany: Springer Verlag; p. 107-125).

The study of the molecular characteristic from the hormone and peptides involved in the growth mechanism in the marketable fish and crustacean species is very important to use in the improving the aquaculture.

One example to understand that is the use of gonadotropin release hormone (GnRH) and the antagonist of the dopamine receptor used by Silverstein et al., in 1999 (Silverstein J T., Bosworth B G. and Wolters W R. 1999. Evaluation of dual injection of LHRHa and the dopamine receptor antagonist pimozide in cage spawning of channel catfish *Ictalarus punctatus*. Journal of the World Aquaculture Society. Vol. 30, No. 2, June, 263-268) for the regulation and induction of reproduction in catfish (*Ictalarus punctatus*). This species has high importance in world aquaculture.

Hashizunme et al., reported in 1997 (Hashizume T., Sasaki M., Tauchi S. and Masuda H. 1997. The effect of new growth Hormone-releasing peptide (KP 102) on the release of growth hormone in goats. Animal Science and Technology. Vol. 68, No. 3, March, 247-256) the use of a synthetic peptides for the increase of the productivity in animal farms. They demonstrated the induction of growth hormone in goat by injection with a novel growth hormone release synthetic peptide Insulin had been administrate to fish orally and demonstrated changes in signal of receptor and hormones involved in carp adaptation to different temperatures (Vera M I., Romero F., Figueroa J., Amthauer R., Leon G., Villanueva and Krauskopf M. 1993. Oral administration of insulin in winter-acclimatized carp (*Cyprinus carpio*) induces hepatic ultrastructural changes. Comp. Biochem. Physiol. Vol. 106A, No. 4, 677-682)

In mammals had been tested synthetic variants of the growth hormone release peptide by Patchett et al., in 1995. They probed the peptide MK-0677, designated as potent oral activator of the GH in dogs without effect in the tyrosine and prolactin levels after application (Patchett A A., Nargund R P., Tata J R., Chen M H., Barakat K J., Johnston D B R., Cheng K., Chan W W S., Butler B., Hickey G., Jacks T., Schleim K., Pong S S., Chaung L Y P., Chen H Y., Frazier E., Leung K H., Chiu S H L. and Smith R G. 1995. Proc. Natl. Acad. Sci. USA. Vol. 92, 7001-7005)

Other application of the growth hormone release hormone had been developed in cattle to increase the milk production, taking into account the stimulation in milk production produced by the increased level of the circulating GH (Soliman E B., Hashizume T., Ohashi S. and Kanematsu S. 1997. Effects of Growth hormone (GH)-releasing hormone and its analogs on GH secretion from cultured adenohypophysial cells in cattle. Domestic animal endocrinology. Vol. 14(1), 39-46)

There are not previous reports of the use of GHRP-6 in fish or crustacean. The use of GHRP-6 in fish and crustacean to stimulate growth, improve the larvae quality, and increase the defense against pathogen agents, the dry weight, the protein concentration and the RNA in muscle of fish and crustaceans reported in this document comprise a solution for improve the productivity in the aquatic organisms culture.

There are preliminary results in the genetic breeding of some shrimp species like *Penaeus japonicus* and *Litopenaeus vanname* but these are not enough because the lack of knowledge about the genetic and biochemistry of these organisms (Benzie, J. A. H., 1998. Penaeid genetics and biotechnology. Aquaculture 164, 23-47 and Fjalestadl, K. T., Carr, W. H., Lotz, J. L., Sweeney, J. N., 1999. Genetic variation and selection response in body weight and diseases resistance in the Pacific White Shrimp *Penaeus Õannamei*. Aqucculture 173, 10, Abstract only). It is very important to apply the biotechnology, molecular biology, genetic engineering and biochemistry to the culture of shrimp to improve the productivity (Bachere, E., Mialhe, E., Noel, D., Boulo, V., Morvan, A., Rodriguez, J. (1995) Knowledge and research prospects in marine mollusc and crustacean immunology. *Aquaculture*. 132, 17-32).

This invention support that the GHRP-6 alone is able to stimulate growth, improve the larvae quality, and increase the defense against pathogen agents, the dry weight, the protein concentration and the RNA in muscle of fish and crustaceans.

ESSENCE OF THE INVENTION

The essence and novelty of this invention support that the peptide GHRP-6 alone is able to stimulate growth, improve the larvae quality, and increase the defense against pathogen agents, the dry weight, the protein concentration and the RNA in muscle of fish and crustaceans. The secretagogue GHRP-6 alone is able to stimulate growth orally, by injection or immersion in fish and crustaceans.

DETAILED DESCRIPTION OF THE INVENTION

Firstly, the biological activity to promote the releasing of GH of the hexapeptide GHRP-6 (Growth hormone release peptide), with the sequence corresponding to: His-D-Trp-Ala-Trp-D-Phe-Lys-$NH_2$, (SEQ. ID. NO.: 1), was demonstrated like in mammals and birds (Bowers C, Momany, G, Reynolds G and A. Hong. 1984. On the in vitro and in vivo activity of a new synthetic hexapeptide that acts on the Pituitary to specifically release growth hormone. Endocrinology. 114: 1537-45).

As the teleost GH levels are very variable along the day serum samples were taken before the treatment and after that per each fish. The result shows there was an increased in serum GH levels in the time coursing experiment at 15 min after the intraperitoneal hexapeptide treatment. In teleost fish, as in other vertebrates, the growth promoting action of GH is mainly mediated by the induction of IGF. The level of hepatic IGF mRNA increased significantly in response to intraperitoneal injection of GHRP-6 at 30 min backing to the normal value during six hours after injection. (Example 1).

It was demonstrated that the peptide GHRP-6 alone exert a similar biological function in fish than in mammals and birds suggesting that this mechanisms is similar.

In vivo, the role of the GHRP-6 in controlling body growth in freshwater juvenile tilapia was assessed. The treatment with GHRP-6 using different ways of administration significantly stimulated growth in comparison with control group as determined by the increase in growth rate after three weeks of treatment by three different ways of administration: a) Intraperitoneal injection, b) Oral and c) Immersion. (Example 2)

In 1 g tilapia larvae were demonstrated the effect of the hexapeptide GHRP-6 applied by immersion in the increasing of pathogen resistance and muscle quality. (Example 3). The result showed that the tilapia groups treated with the GHRP-6 increased the weigh and protein concentration and decrease the intensity and extension of pathogen invasion and the water content of the muscle. This results suggest the positive effect of the hexapeptide in the protein synthesis.

GHRP-6 was assayed in shrimp *Litopenaeus Schmitt* demonstrate that alone was able to improve the growth rate in crustaceans by different way of administration: a) Intraperitoneal injection, b) Oral and c) immersion. (Example 4)

The hexapeptide was assayed in shrimp *Litopenaeus schmitti* demonstrate that alone was able to improve the growth rate by the application of 4-immersion bath in different larvae stage. The quality of the larvae at the final of the larvae culture cycle was improved by the peptide. The larvae showed significantly increase in weigh, size, number of gill ramifications, modification of rostral bone, protein concentration and RNA in the muscle. It was evident an increased metabolic activity.

The improved quality of the larvae was maintain by the adults shrimp yield an increase biomass and more uniformity in the weigh and size of the animals. GHRP-6 was able to promote the growth rate in adult shrimp *Litopenaus schmitti*, by intramuscle injection. After 15 days of the injection of the GHRP-6 the group of animals treated showed an increase between 100% to 150% respect to a control group. (Example 5)

The secretagogue GHRP-6 administrated orally in the diet or encapsulated in *Artemia salina* improved the growth rate in shrimp *Litopenaeus Schmitt*, between 30% to 40% respect a control group. (Example 6)

EXAMPLES

Example 1

Biological Activity Demonstration of the GHRP-6 in Fish

Fifteen tilapias with average weight 71±28 g were used for the experiment. The GHRP-6 was injected with hexapeptide at 0.1 µg/gbw. The liver and blood samples were drawn before the treatment and 15 min, 30 min, 1 h and 6 h after the peptide injection (three animals per group). The serum and liver sample were collected and stored at −70° C. until used for total RNA isolation and Northern blot analysis. A serum sample was also taken before the treatment in all animals.

Northern blot analysis was used to measure the relative IGF mRNA levels in tilapia injected with the peptide. Total RNA was purified from liver samples as described by Chomczynski and Sacchi (Chomczynski P, Sacchi N. Single step method of RNA isolation by acid guanidium thiocyanate-phenol-chloroform extraction. Anal Biochem 1987; 162:156-59). Twenty µg of RNA were fractionated on 1% formaldehyde agarose gels and transferred to nylon membranes (Hybond N, Amersham UK) and hybridized with a tilapia IGF-I cDNA probe and subsequently rehybridized with a human gliceraldehyde 3 phosphate dehydrogenase cDNA (GAPDH, kindly given by Dr. Bryan Williams, Cleveland Foundation, OH, USA) to normalize the signals. Hybridization signals were quantified by digital image processing of scanned gels with a Hewlett Packard Scanjet Plus scanner. Images were processed with the Bandleader computer program. Results were expressed in RNA arbitrary units.

Serum GH levels were determined by ELISA using two monoclonal antibodies against tilapia GH (Muñoz et al, in preparation).

Figure 1:
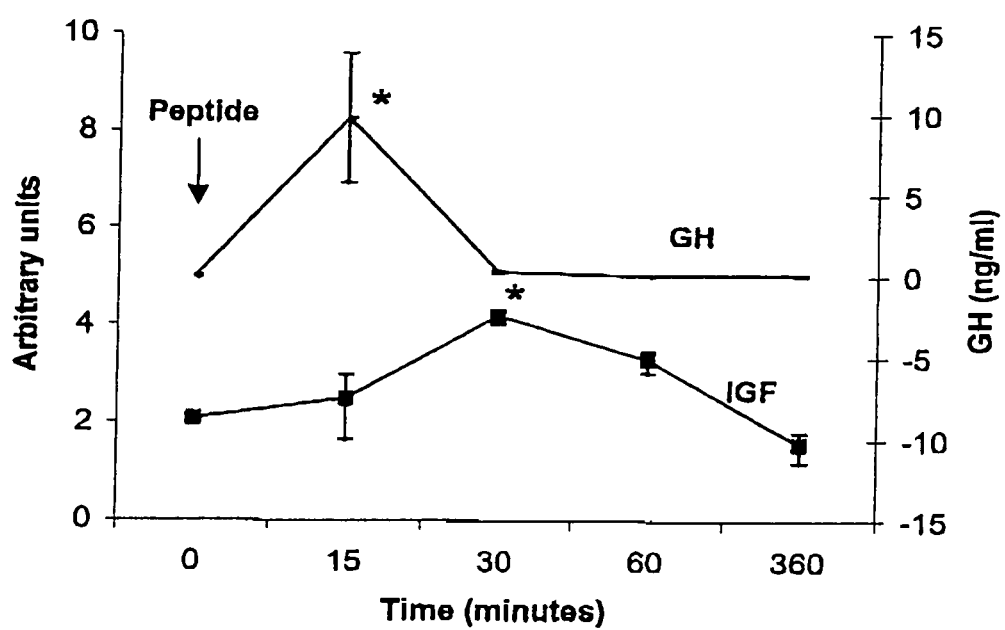
FIG. 1. Tilapia IGF mRNA levels and serum GH levels in juvenile tilapia injected with the GHRP-6 peptide. Each group intraperitoneally injected was of three animals. Liver and serum sample were taken 15 min, 30 min, 1 h and 6 h post injection. A sample serum was taken from each animal before the treatment. *Significantly different from the control group ($p<0.001$ ANOVA, Duncan test).

As the teleost OH levels are very variable along the day serum samples were taken before the treatment and after that per each fish. FIG. 1 shows there was an increased in serum GH levels in the time coursing experiment at 15 min after the intraperitoneal hexapeptide treatment. In teleost fish, as in other vertebrates, the growth promoting action of GH is mainly mediated by the induction of IGF. The level of hepatic IGF mRNA increased significantly in response to intraperitoneal injection of GHRP-6 at 30 min backing to the normal value during six hours after injection. (FIG. 1)

Example 2

Growth Promoting Activity of GHRP-6 in Juvenile (*Oreochromis* sp) Tilapia 2.1 Intaperitoneal Injection Juvenile hybrid tilapia (*Oreochromis aureus*) supplied by the Aquadique Aquaculture Station (Havana, Cuba) were acclimated in a 500 litters tank with re-circulating freshwater at 25° C. with constant photoperiod (14 hours light and 10 hours darkness) and fed with commercially prepared pellets (CENPALAB, Havana, Cuba). Daily rations equivalent to 5% of body weight were administered twice a day until they were used in the experiments.

GHRP-6 (BACHEM, Switzerland) was diluted in PBS and injected twice a week during three weeks at 0.1 µg per gram of fish body weight (gbw). The peptide was administered to a group of eight male tilapia with average body weight of 61±14.3 g and seven male tilapia with average body weight of 61.41±29.67 g were injected with PBS as a control group.

Body weight in grams was measured weekly. In all the experiments the animals were labeled with microchips (Stoelting Co. Wood Dale, U.S.A.).

Figure 2:
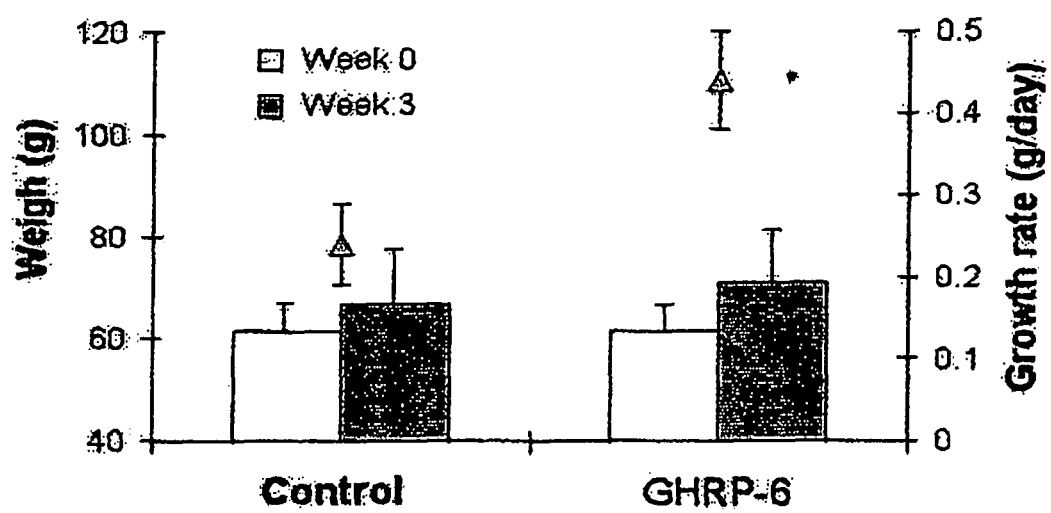
FIG. 2. Effect on body weight and growth rate of GHRP-6 injection in juvenile tilapia over a three-week period. Group of seven tilapia each were intraperitoneally injected twice a week 0.1 µg of peptide/gbw with a control group receiving saline vehicle. *Significantly different from the control group ($p<0.029$; Student's t test) Bars indicate standard error. Triangle indicate the mean growth rate.

The treatment with GHRP-6 by intraperitoneal administration significantly stimulated growth as determined by the increase in growth rate after three weeks of treatment intraperitoneal injections of 0.1 µg/gbw. (P<0.05) (FIG. 2)

2.2 Oral Administration

Other ways of peptide releasing were evaluated orally intubated peptide (FIG. 3) and encapsulated intubated peptide (FIG. 4), the growth rate was also statistically significantly in both treatments to compare with the respective controls groups, and in the later case there were statistically differences in the body weight to the end of the treatment. A comparison between both orally intubated treatment showed a higher body weight gain with the encapsulated peptide treatment one. (P<0.05)

Figure 3:
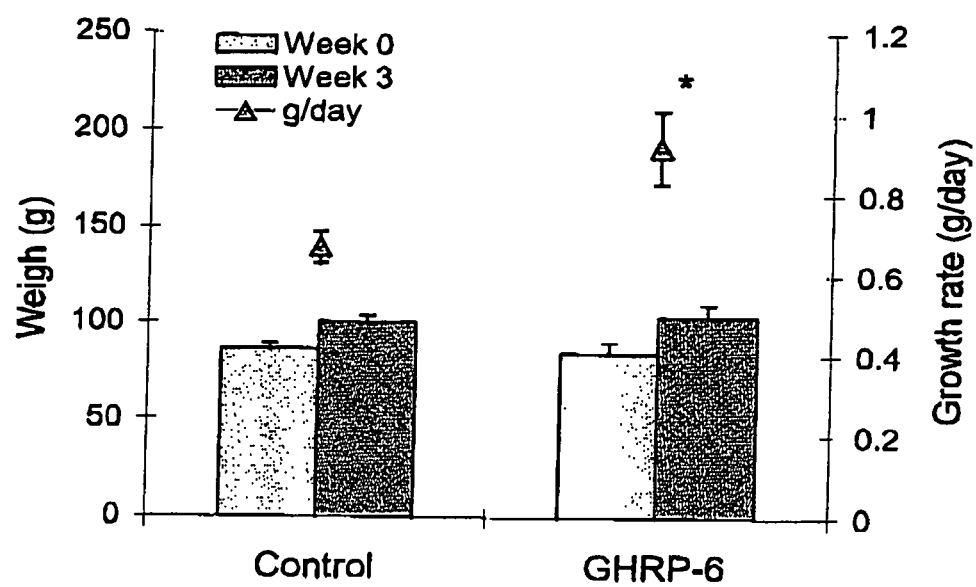
FIG. 3. Effect on body weight and growth rate of GHRP-6 non encapsulated orally intubated in juvenile tilapia over a three week period. Group of five tilapia were treated twice a week 0.1 µg of peptide/gbw with a control group receiving saline vehicle. *Significantly different from the control group ($p=0.015$, Multiple Range Test) Bars indicate standard error. Triangle indicate the mean growth rate.

GHRP-6 peptide was diluted in phosphate buffered saline (PBS) and administered through a plastic tube to the pharyngeal cavity to a group of seven male tilapia with average body weight 87.22±14.1 g. PBS was delivered to the control group (n=7, all male tilapia) with average weight 89.22±7.66 g. The treatment was done twice a week during three weeks at 0.1 µg/gbw. Body weight in grams was measured weekly. (FIG. 3)

Figure 4:
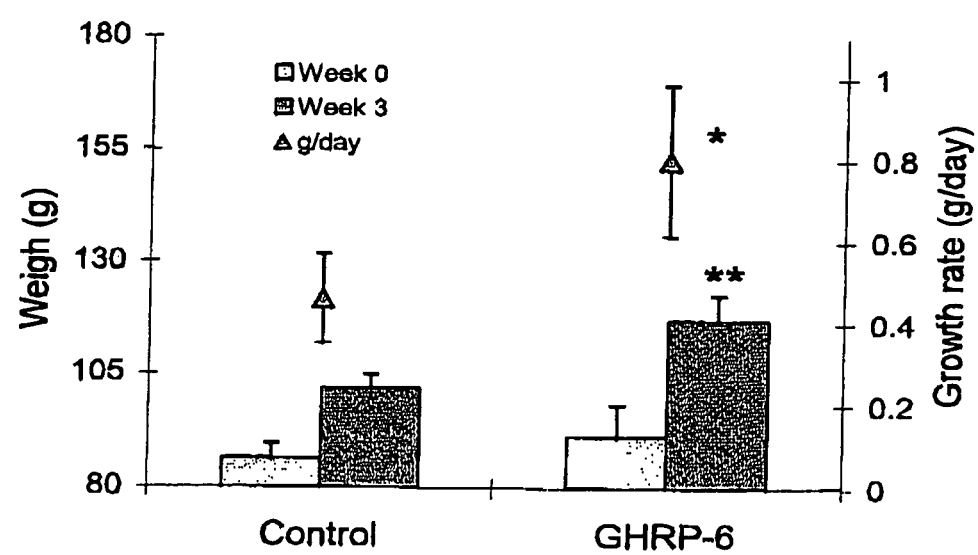
FIG. 4. Effect in juvenile tilapia over a three-week period treated orally with GHRP-6 encapsulated on body weight and growth rate. Group content five tilapia was treated twice a week 0.1 µg of peptide/gbw with a control group receiving saline vehicle. *Significantly different from the control group ($p=0.007$, Multiple Range Test) Bars indicate standard error. Triangle indicates the mean growth rate.

For the encapsulation of peptide the capsules were obtained as previously reported by Knorr et al., 1988; using chitosan and alginic acid encapsulated peptide. The hexapeptide GHRP-6 was administered through a plastic tube to the pharyngeal cavity to seven male tilapia with average body weight 89.09±8.38 g. Polymer beads without peptide were administered to seven male tilapia with average weight 89.86±13.54 g as a control group. The treatment was performed twice a week at 0.14 µg/gbw. (FIG. 4)

Example 3

Growth Promoting Activity of GHRP-4 in Juvenile (*Oreochromis* sp) Tilapia by Immersion Tilapias (*Oreochromis aureus*) of 1.5 g of mean weigh were treated by immersion with two different doses of GHRP-6 (10 µg/100 ml and 100 µg/100 ml). A similar control group was treated with physiological solution.

In the experiment was measured the weigh (Table 1), biochemical blood parameters (Table 2), number of parasite in gill (*Trichodinicos* (Table 3) y *Helmintos mongeneos* (Table 4)) and humidity and protein concentration in muscle Fifteen animals per group (3×) with mean weigh of 1 g were selected for the assay. In 9 tank of 40 liters were developed the experiment. One a week application was done for 45 days.

The Groups and Doses were Distributed as Followed:

Group I 10 µg/100 ml (Treatment 1)

Group II 100 µg/100 ml (Treatment 2)

Group III Control (Physiological solution)

TABLE 1

Mean weigh measured in the different groups of tilapia treated with GHRP-6 by immersion

| Treatment | n | Mean weigh (g) ± DS | Comparison between groups | Statistically difference |
|---|---|---|---|---|
| Grupo I 10 µg/100 mL | 25 | 4.56 ± 1.07 | I-II | 0.01454 |
| Grupo II 100 µg/100 mL | 25 | 4.54 ± 1.38 | II-III | 1.07177* |
| Grupo III Saline solution | 25 | 3.47 ± 1.52 | III-I | 1.08632* |

*Significantly difference. Multiple rank tests

TABLE 2

Hematocrite values in the different groups of tilapia treated with GHRP-6 by immersion

| Treatment | n | Mean weigh (g) ± SD | Comparison between groups | Statistically difference |
|---|---|---|---|---|
| Grupo I 10 µg/100 mL | 15 | 27.46 ± 4.53 | I-II | (2.4)* |
| Grupo II 100 µg/100 mL | 15 | 25.06 ± 5.25 | II-III | (1.0)* |
| Grupo III Saline solution | 15 | 26.46 ± 4.08 | III-I | (1.4)* |

*There is not significantly difference. Multiple rank tests

TABLE 3

Invasion intensity (I) and extension (E) in the tilapia treated with GHRP-6 by immersion for the protozoo *Trichodina* sp.

| Treatment | n | I[a] | E (%)[b] | Comparison between groups | Statistically difference |
|---|---|---|---|---|---|
| Grupo I 10 µg/100 mL | 25 | 7.73 | 100 | I-II | (4.42) |
| Grupo II 100 µg/100 mL | 25 | 2.80 | 84.6 | II-III | (5.84)* |
| Grupo III Saline solution | 25 | 8.76 | 92.30 | III-I | (1.42) |

[a]I: Invasion intensity
[b]E: Invasion extension
*Significantly difference. Multiple rank tests

TABLE 4

Invasion intensity (I) and extension (E) in the tilapia treated with
GHRP-6 by immersion for Helmintos monogeneos in the gill per fish.

| Treatment | n | I[a] | E (%)[b] | Comparison between groups | Statistically difference |
|---|---|---|---|---|---|
| Grupo I. 10 μg/100 mL | 25 | 0.39 | 34.7 | I-II | (0.304) |
| Grupo II 100 μg/100 mL | 25 | 0.66 | 50 | II-III | (0.521) |
| Grupo III Saline solution | 25 | 1.07 | 46 | III-I | (0.826)* |

[a]I: Invasion intensity
[b]E: Invasion extension
*Significantly difference. Multiple rank tests

TABLE 5

Humidity mean values in muscle of the tilapia treated with GHRP-6 by immersion.

| Treatment | n | Mean humidity ± SD (%) | Comparison between groups | Statistically difference |
|---|---|---|---|---|
| Grupo I 10 μg/100 mL | 24 | 82.96 ± 3.63 | I-II | (0.791) |
| Grupo II 100 μg/100 mL | 24 | 83.5 ± 3.31 | II-III | (2.666)* |
| Grupo III Saline solution | 24 | 86.42 ± 3.23 | III-I | (3.458) |

*Significantly difference. Multiple rank tests

TABLE 6

Protein concentration mean values in the tilapia treated with GHRP-6 by immersion.

| Treatment | n | Mean humidity ± SD (%) | Comparison between groups | Statistically difference |
|---|---|---|---|---|
| Grupo I 10 μg/100 mL | 23 | 6.10 | I-II | (1.160)* |
| Grupo II 100 μg/100 mL | 23 | 4.94 | II-III | (1.38)* |
| Grupo III Saline solution | 23 | 3.55 | III-I | (2.64)* |

*Significantly difference. Multiple rank tests

Example 4

Figure 5:
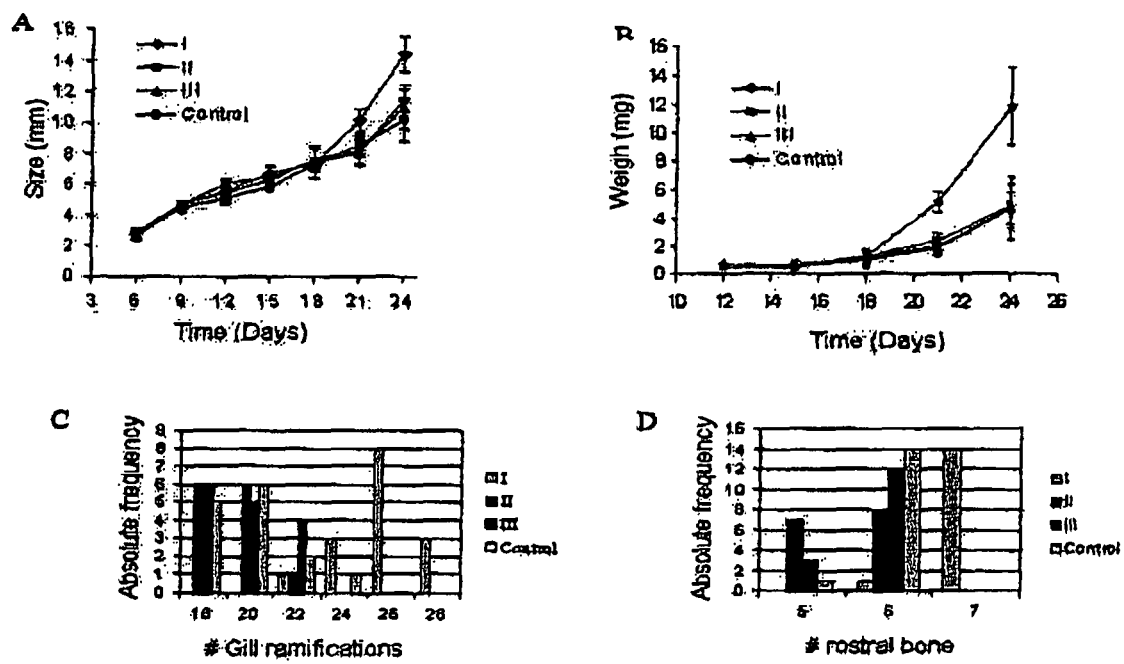
FIG. 5. Growth promoting activity of GHRP-6 in shrimp *Litopenaeus schmitti* treated with GHRP-6 by immersion A: Increase of weight in milligrams of the three groups treated with the GHRP-6 and the control group. B: Increase of size in millimeters of the three groups treated with the GHRP-6 and the control group. C: Absolute frequency distribution of the gill ramifications of the three groups treated with the GHRP-6 and the control group. D: Absolute frequency distribution of the rostral bone of the three groups treated with the GHRP-6 and the control group. I: Group 1: 0.001 mg/L; II: Group 2: 0.01 mg/L; III: Group 3: 0.1 mg/L and Control: 1 mg BSA/L. ***$p<0.001$. Bars indicate standard error (±DS). ANOVA follow by a DUNCAN test were applied for the statically calculation of the difference in weigh and size. Kolmognrov-Smmirnov was applied to rostral bone and gill ramifications.

Growth Promoting Activity of GHRP-6 in Shrimp
*Litopenaeus schmitti* Treated with GHRP-6 by
Immersion Three different doses of GHRP-6 were applied by immersion to groups or shrimp larvae. The application was made each three days. Four applications were made for each group, including one control group receiving bovine serum albumin (BSA). The treatment was made per 1 hour to a concentration of GHRP-6 per liter of seawater as follow:
Group 1: 0.001 mg/L
Group 2: 0.01 mg/L
Group 3: 0.1 mg/L
Group 4: 1 mg of BSA/L The group treated with 0.1 mg/L of GHRP-6 improve the quality of the shrimp larvae showing an increase mean weigh in 153%, mean size in 26%, number of gill ramifications and the number of bone rostral. In all cases the difference was statistical significantly. (FIG. 5)

Figure 6:
FIG. 6. Dry weigh of the shrimp treated with the GHRP-6 and the control group. ***t-test $p<0.001$. Bars indicate standard error.
Figure 7:
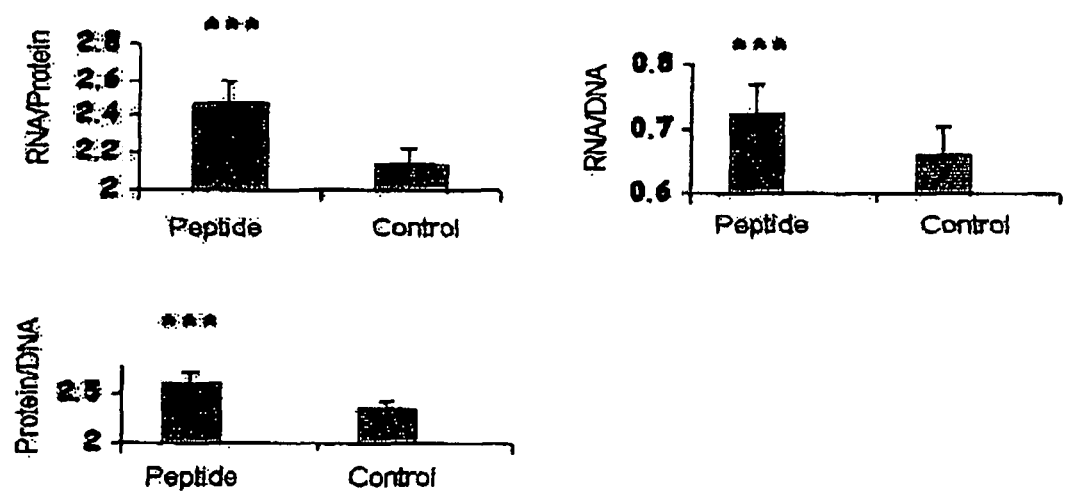
FIG. 7. Relation between RNA, protein and DNA of the shrimp treated with the GHRP-6 and the control group. ***t-test $p<0.001$. Bars indicate standard error.

The entire treated animal showed lower water content in the muscle and increased the value in the relation between RNA/DNA, Protein/DNA suggesting the activation of the metabolism in the muscle of the larvae by the GHRP-6. (FIGS. 6 and 7)

These results are very important taking into account the relevancy of the quality of the larvae for the culture of crustaceans.

Figure 8:
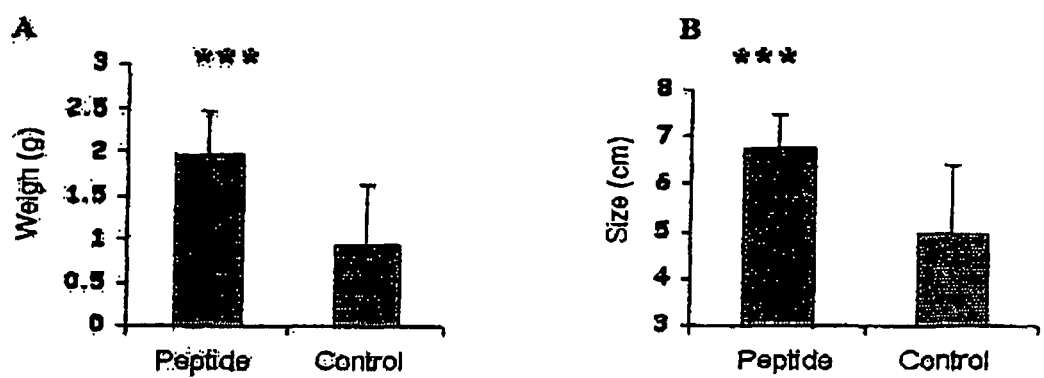
FIG. 8. Growth rate of larvae shrimp *Litopeneaus schmitti* in production conditions treated with GHRP-6 by immersion. The experiment was follow by six week. ***t-test $p<0.001$. Bars indicate standard error

In production condition the survival rate of the larvae was increased in 20% in the group treated with the GHRP-6 in comparison with the non-treated group. In the same assay the weigh was increase in 115% and the size in 37%. On the other hand the uniformity of the animals was higher in the group treated with the hexapeptide and the variation coefficient was lower in weigh and size (FIG. 8).

Example 5

Growth Promoting Activity of GHRP-6 in Adult
Shrimp *Litopenaeus schmitti* Treated with GHRP-6
by Intramuscle Injection Injection of 50 μl of the GHRP-6 was made between the second and third abdominal segment in adult shrimp of approximately 15 g. One injection each three days was made with the doses of 1 μg of GHRP-6 per grams of weigh of the shrimp. One control group was injected with BSA at the same concentration. Fifteen animals per group were used. The variable measured were weigh and size and the groups treated with peptide. Significantly difference were observed in the groups of animals treated with the GHRP-6 ($p<0.001$) with an increase between 100%-150%.

The animals were maintained in a net (0.8 cm) into a pond. The pond water temperature was 25° C. and the photoperiod natural.

Example 6

Growth Promoting Activity of GHRP-6 in Shrimp
*Litopenaeus schmitti* Treated with GHRP-6 Included
in the Diet The GHRP-6 was included at 1% in the diet of post larvae shrimp *Litopenaeus schmitti*. The peptide was encapsulate by a method reported by Knorr (Knorr D. and M. Daly. (1988). Mechanics and diffusional changes observed in multi-layer chitosan/alginate coacervate capsules. Process Biochemistry; 48-50). One control group was feed with the diet with 1% of BSA. The mean weigh and size were measured at the beginning and at the end of the experiment. The duration of the experiment was 30 days.

The GHRP-6 included in the diet of the post larvae of shrimp improves the growth rate in 30%-40% respect to a control group. Significantly difference. ($p<0.001$).

6.1. *Artemia Salina* Encapsulation

The GHRP-6 was encapsulated in Antemia to feed the post larvae of shrimp *Litopenaeus schmitti* and *Litopenaeus vanamei*. For the encapsulation the peptide was added in *Artemia salina* in a concentration of 10 mg/L for an hour and the artemia was harvested and washed in saline solution. Four time a days were feed the post larvae of shrimp during a month. The control group received BSA encapsulated in artemia at the same concentration.

The GHRP-6 encapsulated in *artemia salina* improve the weigh and size of the shrimp larvae in 30%-40%. Respect to the control group. Significantly difference. ($p<0.001$).

The invention claimed is:

1. A method for stimulating resistance to diseases in fish and crustaceans comprising administering to said fish and crustaceans an effective amount of GHRP-6 consisting of the SEQ ID NO: 1, wherein said GHRP-6 is administered:
(a) by adding GHRP-6 to feed of said fish and crustaceans,
(b) by injection, or
(c) by immersion.

2. A method according to claim 1, wherein said GHRP-6 is administered by adding GHRP-6 to feed of said fish and crustaceans.

3. A method according to claim 1, wherein said effective amount of GHRP-6 is 0.01-50 µg of GHRP-6 per gram wet weight of said fish and crustacean.

4. A method according to claim 1, wherein said GHRP-6 is administered by injection.

5. A method according to claim 1, wherein said GHRP-6 is administered by immersion.

6. A method according to claim 5, wherein said immersion is in freshwater containing 10-500 µg GHRP-6 per liter of freshwater.

7. A method according to claim 5, wherein said immersion is in seawater containing 10-500 µg GHRP-6 per liter of seawater.

8. A method according to claim 5, wherein said immersion occurs at an interval of 1 to 7 days.

9. A method according to claim 2, wherein said feed is encapsulated.

10. A method according to claim 2, wherein said feed is provided to said fish and crustaceans at an interval of 1 to 7 days.

11. A method according to claim 1, wherein said fish is tilapia *Oreochromis* sp.

12. A method according to claim 1, wherein said fish is *Salmon* sp.

13. A method according to claim 1, wherein said crustacean is selected from the group consisting of *Litopenaeus schmitti, Litopeneaus vanamei, Penaeus* sp. and combinations thereof.

14. A method for decreasing the intensity and extension of pathogen invasion in fish and crustaceans comprising administering to said fish and crustaceans an effective amount of GHRP-6 consisting of the SEQ ID NO: 1, wherein said GHRP-6 is administered:
(a) by adding GHRP-6 to feed of said fish and crustaceans,
(b) by injection, or
(c) by immersion.

* * * * *

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial sequence
<220> FEATURE:
<223> OTHER INFORMATION: synthetic peptide GHRP-6
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MOD_RES
<222> LOCATION: (6)..(6)
<223> OTHER INFORMATION: AMIDATION

<400> SEQUENCE: 1

His Trp Ala Trp Phe Lys
1               5
```